United States Patent
Matsuura et al.

(10) Patent No.: US 7,976,782 B2
(45) Date of Patent: Jul. 12, 2011

(54) EXTERIOR PANEL FOR RECEIVING AROMATIC SUBSTANCE, AND MOBILE TERMINAL USING EXTERIOR PANEL FOR RECEIVING AROMATIC SUBSTANCE

(75) Inventors: Iwao Matsuura, Kanagawa (JP);
Junichi Yasuno, Kanagawa (JP);
Akihiro Miyashita, Kanagawa (JP);
Koji Taniguchi, Kanagawa (JP);
Akitoshi Mori, Kanagawa (JP); Saori Suzuki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 618 days.

(21) Appl. No.: 12/095,763

(22) PCT Filed: Dec. 9, 2005

(86) PCT No.: PCT/JP2005/022640
§ 371 (c)(1),
(2), (4) Date: Jun. 2, 2008

(87) PCT Pub. No.: WO2007/066408
PCT Pub. Date: Jun. 14, 2007

(65) Prior Publication Data
US 2009/0126839 A1 May 21, 2009

(51) Int. Cl.
*A61L 9/00* (2006.01)
(52) U.S. Cl. ............... 422/120; 422/123; 239/57
(58) Field of Classification Search ........... 422/120, 422/123; 239/57, 274
See application file for complete search history.

(56) References Cited

U.S. PATENT DOCUMENTS

| | | | | |
|---|---|---|---|---|
| 4,184,612 A | * | 1/1980 | Freyre | 222/639 |
| 5,257,421 A | * | 11/1993 | Rose et al. | 4/214 |
| 2004/0204043 A1 | | 10/2004 | Wang et al. | |

FOREIGN PATENT DOCUMENTS

| | | |
|---|---|---|
| EP | 1 441 490 A1 | 7/2004 |
| JP | 2002-76734 A | 3/2002 |
| JP | 2002-290525 A | 10/2002 |
| JP | 2002-290526 A | 10/2002 |
| JP | 2003-60738 A | 2/2003 |
| JP | 2003-143280 A | 5/2003 |
| JP | 2004-157856 A | 6/2004 |
| JP | 2004-159908 A | 6/2004 |
| JP | 2004-254026 A | 9/2004 |
| WO | WO 03/026706 A2 | 4/2003 |
| WO | WO 2004/105816 A1 | 12/2004 |

OTHER PUBLICATIONS

Supplementary European Search Report for Application No. EP 05 81 4752, Publication Date Jul. 2, 2009, Panasonic Corporation.
International Search Report for PCT/JP2005/022640, dated Feb. 21, 2006.

* cited by examiner

*Primary Examiner* — Sean E Conley
(74) *Attorney, Agent, or Firm* — RatnerPrestia (57) ABSTRACT

A folding type portable telephone in which a first housing and a second housing are fixed by a hinge includes a face panel fixed to the first housing and aromatic substances are accommodated inside the face panel. When the hinge is rotated, the aromatic substances are released in conjunction with the operation of opening the folding type portable telephone from the closed state. Furthermore, a sounding body is operated at a frequency of strongly generating an air vibration at a time defined in advance by timer control, so that fragrance of the aromatic substances is released outward by the air vibration of the sounding body. The fragrance corresponding to TPO can be generated from the face panel of the portable telephone.

1 Claim, 11 Drawing Sheets

EXTERIOR PANEL FOR RECEIVING AROMATIC SUBSTANCE, AND MOBILE TERMINAL USING EXTERIOR PANEL FOR RECEIVING AROMATIC SUBSTANCE

This application is a U.S. National Phase Application of PCT International Application PCT/JP2005/022640.

TECHNICAL FIELD

The present invention relates to a mobile terminal such as a portable telephone, a PDA, a music player, and a game machine with a removable face panel, in particular, to a mobile terminal with aroma releasing function using an aromatic substance accommodating face panel.

BACKGROUND ART

A design of a removable face panel used in a portable telephone, a PDA, a music player, a game machine, or the like of the prior art may be changed by being replaced to be visually entertaining. A technique of generating fragrance from the portable telephone has been conventionally proposed. A technique in which an open/close operation of an aroma releasing port is carried out by extension and accommodation of a rod antenna of the portable telephone, where the aroma releasing port is opened to release the fragrance when the rod antenna is extended upward, and the aroma releasing port is closed to prevent fragrance from being released when the rod antenna is accommodated in a main body is disclosed in, for example, Unexamined Japanese Patent Publication No. 2002-76734.

In a folding type portable telephone, a technique in which a small hole opened in a member configuring a hinge mechanism is exposed by opening a lid body thereby diffusing aroma of an aroma member filled inside the member towards a user of the portable telephone is disclosed in, for example, Unexamined Japanese Patent Publication No. 2002-290525, or the like.

Furthermore, a technique having characteristics in that a flow path for flowing fragrance of the aromatic substances from openings of a speaker or a microphone arranged inside a housing is arranged inside the housing, and in that an aroma material is arranged adjacent to a battery to promote an aroma effect by heat generation of the battery is disclosed in, for example, Unexamined Japanese Patent Publication No. 2004-254026, or the like.

However, in the technique disclosed in Unexamined Japanese Patent Publication No. 2002-76734, a structure in that aroma is only released when the rod antenna is extended is convenient in that natural release of aroma can be suppressed, but the operation of extending and accommodating the rod antenna is bothersome. The above structure is often not adopted in recent years with increase terminals in which the antenna is built in the housing with high regard for designability.

In the technique disclosed in Unexamined Japanese Patent Publication No. 2002-290525, a function excelling in operability of controlling aroma with the open/close operation of the hinge is provided, but the fragrance attaches to the inside of the housing by arranging the aroma member inside the hinge, thereby influencing the durability of electronic components to which the components of the aroma member come close.

In the technique disclosed in Unexamined Japanese Patent Publication No. 2004-254026, the fragrance attaches to the inside of the housing by arranging the aroma member adjacent to the battery, thereby influencing the durability of electronic components to which the components of the aroma member come close.

Thus, there is a problem in that a mobile terminal with aroma releasing function in which fragrance is prevented from attaching to the inside of the housing, the influence of the aroma member on the electronic components inside the housing is reduced as much as possible, and the aroma can be changed according to TPO is not realized.

DISCLOSURE OF THE INVENTION

In order to solve the above problems, according to an aromatic substance accommodating face panel of the present invention, the face panel has a hollow structure; an open/close port for replacing a content of the hollow structure, an aroma releasing hole for releasing the aroma, and a fixing means for removably fixing to a housing of the mobile terminal are formed in the face panel; and aromatic substances are accommodated in a space portion of the hollow structure.

According to such a configuration, not only can the face panel be replaced according to TPO, but the aromatic substances can also be changed.

In a mobile terminal using the aromatic substance accommodating face panel of the present invention, a first housing and a second housing are rotatably connected to each other by a hinge; a projection is formed on the hinge; an aromatic substance accommodating face panel to be removably attached to the first housing or the second housing is arranged, the aromatic substance accommodating face panel having a hollow structure; an aroma releasing hole for releasing aroma is formed and an open/close valve for opening and closing the hollow structure with respect to an external space is arranged on a panel surface; and the hinge rotates, so that the projection of the hinge controls the open/close valve of the aromatic substance accommodating face panel to release the aroma from the aroma releasing hole at the surface of the aromatic substance accommodating face panel.

Furthermore, in a mobile terminal using the aromatic substance accommodating face panel of the present invention, a first housing and a second housing are rotatably connected to each other by a hinge; an aromatic substance accommodating face panel to be removably attached to the first housing is arranged, the aromatic substance accommodating face panel having a hollow structure; an aroma releasing hole for releasing aroma is formed on the first housing side of the aromatic substance accommodating face panel; a pass-through hole passing through the first housing is formed on the side facing the aroma releasing hole of the aromatic substance accommodating face panel of the first housing, the pass-through hole of the first housing being spatially independent from other electronic components; and the hinge is rotated so that the hollow structure of the aromatic substance accommodating face panel opens to an external space when the housings are opened through the pass-through hole of the first housing, and closes to the external space when the housings are closed.

According to the above configuration, the aromatic substances can be released in conjunction with the operation of opening the folding type mobile terminal from the closed state, and the aromatic substances can be prevented from being released in conjunction with the operation of closing the folding type mobile terminal from the opened state.

In a mobile terminal using the aromatic substance accommodating face panel of the present invention, a sounding body is arranged in a housing; an air vibration transmitting hole for transmitting an air vibration of the sounding body is formed on a surface of the housing including the sounding body; an aromatic substance accommodating face panel to be removably attached to the housing is arranged, the aromatic substance accommodating face panel having a hollow structure; an air vibration transmission hole for transmitting the air vibration is formed on the surface facing the housing of the aromatic substance accommodating face panel; an aroma releasing hole for releasing aroma to an external space is formed on the surface opposite to the surface facing the housing; the air vibration transmitting hole of the housing and the air vibration transmission hole for transmitting the air vibration of the aromatic substance accommodating face panel are spatially bonded; and the vibration of the sounding body in the housing is transmitted from the air vibration transmitting hole of the housing to the air vibration transmission hole of the aromatic substance accommodating face panel so that the aroma is released to the external space from the aroma releasing hole of the aromatic substance accommodating face panel.

According to this configuration, the aromatic substances are released in conjunction with the operating state of the sounding body, and the aromatic substances are not released in conjunction with the stopped state of the sounding body.

Therefore, the present invention prevents the body of the housing from being attached with fragrance by placing the aromatic substances inside the face panel to be removably attached to the housing. Different fragrances of the aromatic substances can be enjoyed by replacing the face panel portion. In the folding type mobile terminal, the aromatic substances are released when the housings are opened. Furthermore, in the mobile terminal that utilizes vibration of the sounding body, the aromatic substances are released when the sounding body operates. Thus, the aromatic substances can be released at a more effective timing by controlling the release state of the aromatic substances, and the life span of the aromatic substances can be extended.

REFERENCE MARKS IN THE DRAWINGS 101, 201, 401, 501, 601, 701 face panel
102, 202, 402, 502, 602 upper housing
103, 203, 403, 503, 603 hinge
104, 204, 404, 504, 604 lower housing
105 design sheet accommodating unit
106, 206, 406, 506, 606 aromatic substance accommodating unit
107 hinge projection
108 aroma releasing open/close valve
109, 209, 417, 519, 623, 720, 723 aroma releasing hole
110 spring
111 spring press fixing part
210, 624 pass-through hole
211, 411, 511, 611 spacer
212, 412, 512, 612 aromatic substances
225 light emitting body
226 aromatic substances transmissive mesh sheet
313, 713 aromatic substance insertion port 324, 724 aromatic substance insertion lid
114, 314, 614, 714 screw hole
416, 520, 622, 719, 722 air vibration transmission hole
418, 518, 618 sounding body
419 aromatic substance shield sheet
420, 625 air vibration transmitting hole
521 air vibration transmitting space

PREFERRED EMBODIMENTS FOR CARRYING
OUT OF THE INVENTION

The embodiments of the present invention will now be described in detail with reference to the accompanying drawings.

First Embodiment

Figure 1:
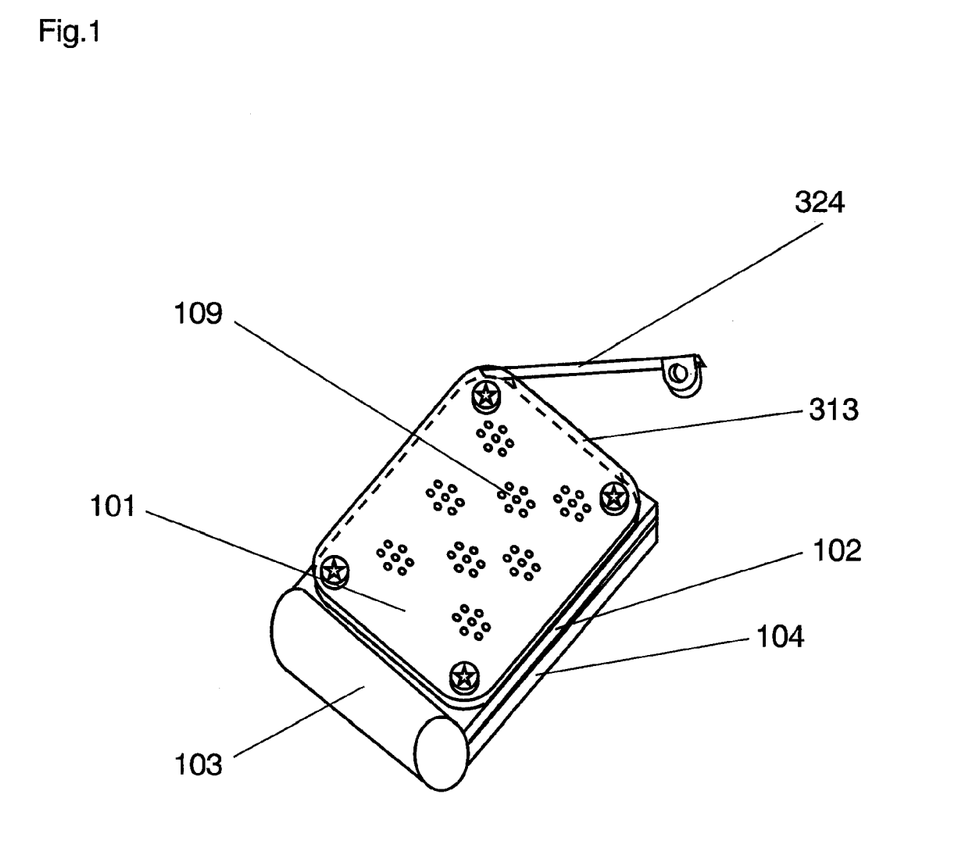
FIG. 1 is a perspective view of a folding type portable telephone according to a first embodiment of the present invention seen in a folded state.

FIG. 1 is an external perspective view showing a first embodiment of a mobile terminal using an aromatic substance accommodating face panel according to the present invention, where the present invention is applied to a folding type portable telephone. The first embodiment describes a folding type portable telephone in which a first housing and a second housing are rotatably connected to each other with a hinge, the first housing being an upper housing and a second housing being a lower housing, where the shape of the portable telephone may be straight type, slide type, rotating type, or the like.

In FIG. 1, upper housing 102 serving as the first housing and lower housing 104 serving as the second housing are supported in a freely rotating manner by hinge 103, where upper housing 102 and lower housing 104 are opened and closed by the rotational movement of hinge 103.

Face panel 101 has a structure of being fixed to upper housing 102 with screws. Face panel 101 has a hollow structure, where the aromatic substances can be easily replaced by forming aromatic substance insertion port 313 that is an open/close port of the face panel at one part on the outer periphery of the side surface. Aromatic substance insertion port 313 is closed by aromatic substance insertion lid 324. The aromatic substances may be in granulated form, paper form, or solid form. Aroma releasing holes 109 of the face panel are on the external side of the portable telephone, and thus can constantly release aroma.

The material of the housing of upper housing 102 and lower housing 104 includes polycarbonate resin (PC resin), polycarbonate ABS resin (PC-ABS resin), or the like; and the material of face panel 101 includes polycarbonate ABS resin (PC-ABS resin), acryl resin (PMMA) and the like.

Figure 2:
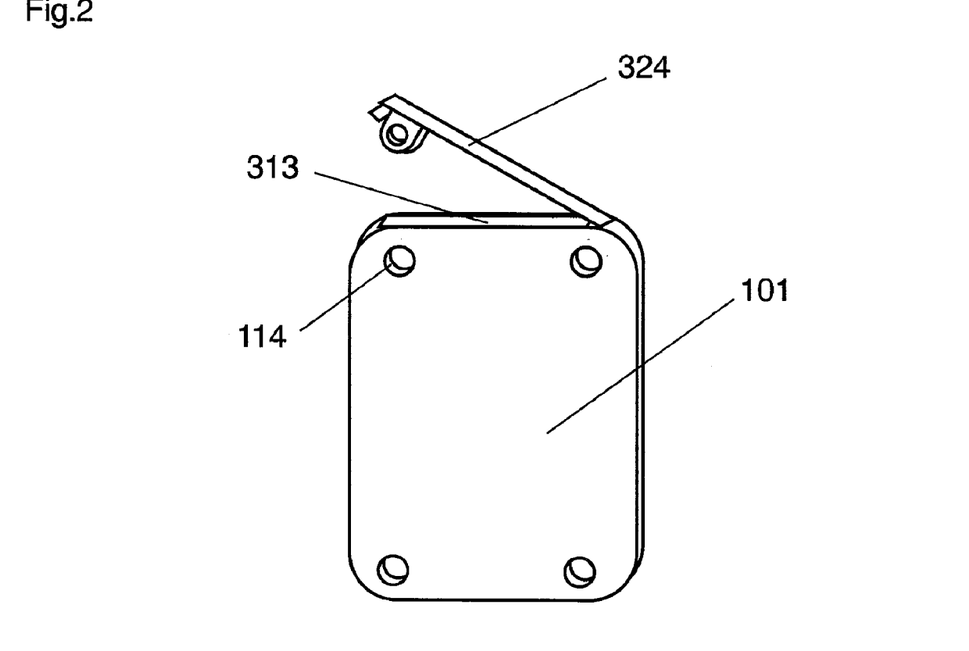
FIG. 2 is an external perspective view of a side facing a housing side of a face panel according to the first embodiment of the present invention.
Figure 3:
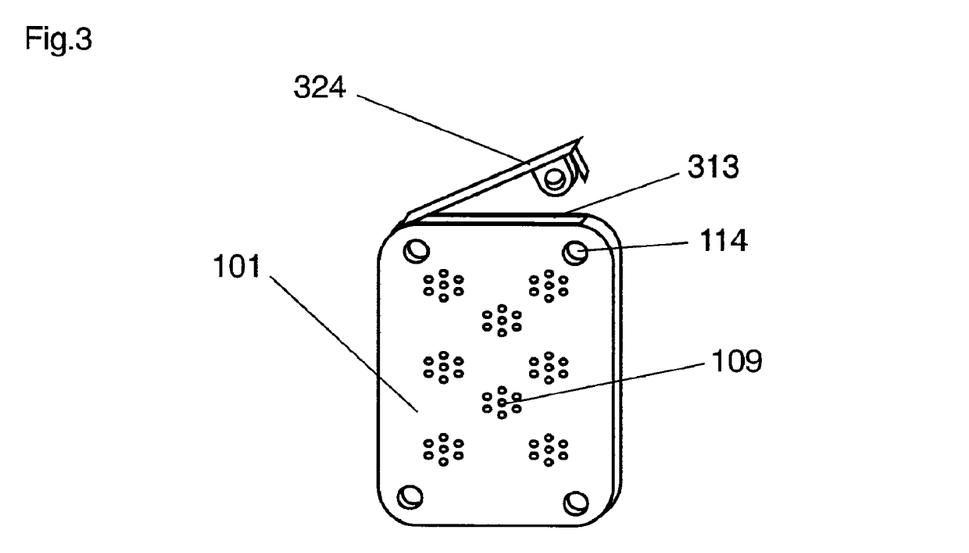
FIG. 3 is an external perspective view of a side facing an external side of the face panel according to the first embodiment of the present invention.

FIG. 2 and FIG. 3 respectively show the front and the back of face panel 101 shown in the first embodiment. FIG. 2 is an external perspective view of the side facing the housing side of face panel 101. The holes for releasing aroma are not formed on the housing side of face panel 101. FIG. 3 is an external perspective view of the side facing the external side of the face panel. Aroma releasing holes 109 for releasing aroma are formed on the external side of face panel 101. Aroma releasing holes 109 of the face panel are attached with tape etc. (not shown) from the outside when not releasing the aroma, and operate the aroma releasing function by stripping the tape.

Aromatic substance insertion port 313 for replacing the aromatic substances and aromatic substance insertion lid 324 are arranged on the periphery of face panel 101. A screw hole commonly fastened with screw hole 114 of face panel 101 is formed in aromatic substance insertion lid 324. The aromatic substance insertion lid of the face panel is prevented from opening when dropped or by impact etc. by commonly fastening the screw hole of aromatic substance insertion lid 324 and the screw hole of the face panel.

Second Embodiment

FIG. 4 to FIG. 8 are views showing a second embodiment of a portable telephone using an aromatic substance accommodating face panel according to the present invention. In the second embodiment of the present invention, the present invention is applied to a folding type portable telephone.

Figure 4:
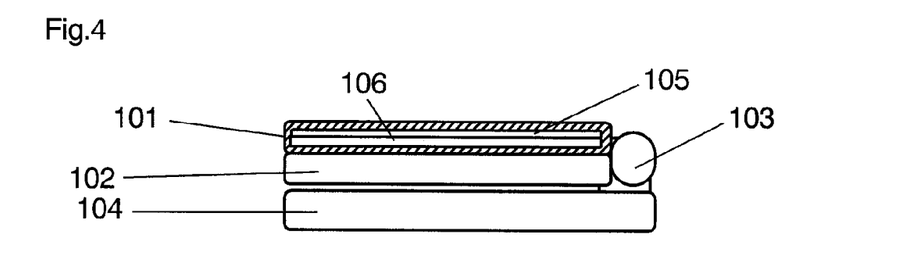
FIG. 4 is a partial cross sectional view of a folding type portable telephone according to a second embodiment of the present invention in a folded state seen from the side.

FIG. 4 is a partial cross sectional view of the folding type portable telephone in a folded state seen from the side surface, where face panel 101 is shown in cross section. In FIG. 4, face panel 101 has a hollow structure, where a space portion is configured by aromatic substance accommodating unit 106 and design sheet accommodating unit 105. Design sheet accommodating unit 105 changes the external image of the folding type portable telephone by inserting a design sheet with patterns and colors using a transparent or a semi-transparent material for face panel 101. Face panel 101 has a structure of being fixed to upper housing 102.

Upper housing 102 serving as the first housing and lower housing 104 serving as the second housing are supported in a freely rotating manner by hinge 103, where upper housing 102 and lower housing 104 are opened and closed by the rotational movement of hinge 103.

Figure 5:
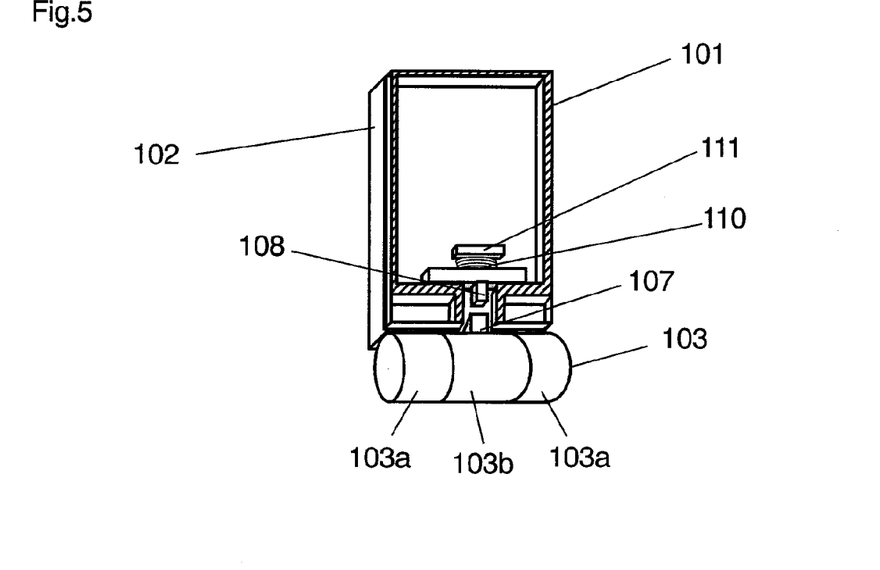
FIG. 5 is a perspective view of the folding type portable telephone according to the second embodiment of the present invention in a folded state seen from above.
Figure 6:
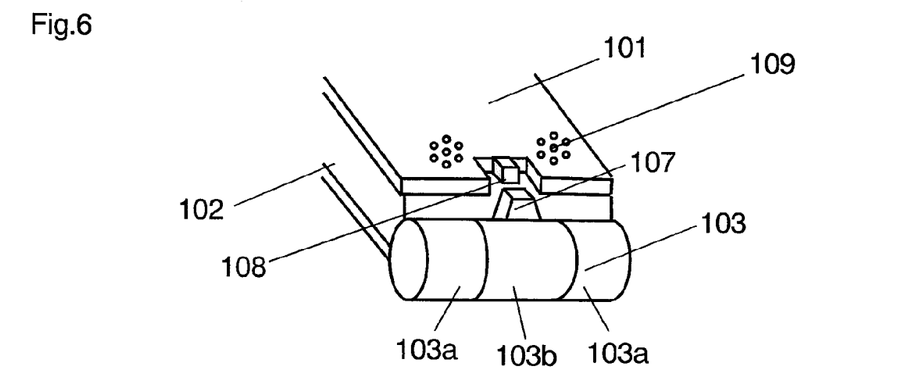
FIG. 6 is a perspective view of a hinge of the folding type portable telephone according to the second embodiment of the present invention in a folded state.

FIG. 5 is a perspective view of the folding type portable telephone in a folded state seen from above. The face panel is shown in cross section so that the inside of face panel 101 can be seen. FIG. 6 is a perspective view of the folding type portable telephone of the present invention in a folded state seen from the side.

In FIG. 5 and FIG. 6, face panel 101 has a structure of being fixed to upper housing 102. Hinge 103 has a rotatable structure. Aroma releasing open/close valve 108 is arranged on face panel 101, and a hole facing aroma releasing open/close valve 108 of face panel 101 is blocked with spring 110 by spring press fixing part 111 of face panel 101. One part 103a of hinge 103 is supported by upper housing 102, and the other parts are supported by lower housing 104 of FIG. 4. Hinge projection 107 is fixed to hinge part 103b on the side supported by the lower housing, where aroma releasing open/close valve 108 of the face panel is pushed by hinge projection 107 and the aroma substances inside face panel 101 is released when upper housing 102 and lower housing 104 of the folding type portable telephone are in the opened state.

Figure 7:
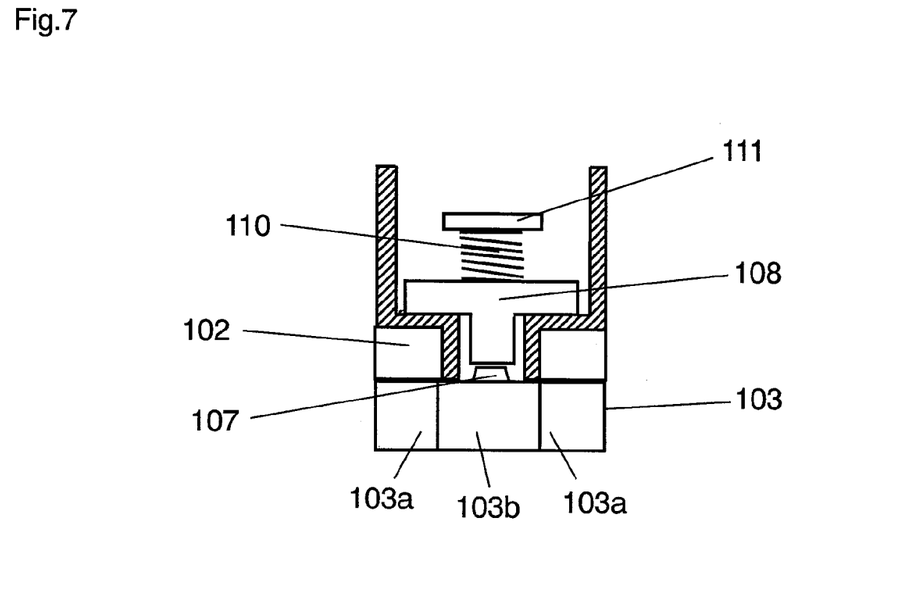
FIG. 7 is a cross sectional view of the folding type portable telephone according to the second embodiment of the present invention in a folded state seen from above.
Figure 8:
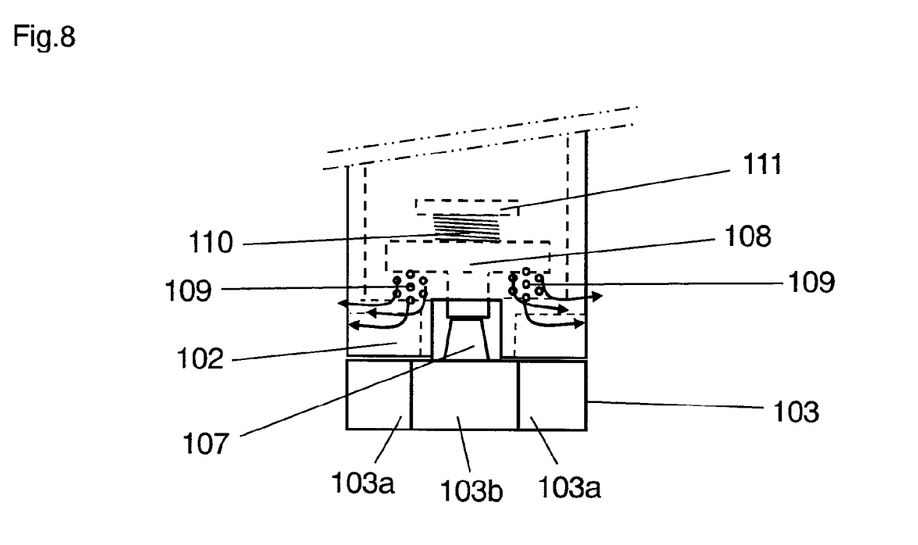
FIG. 8 is a cross sectional view of the folding type portable telephone according to the second embodiment of the present invention in an opened state seen from above.

A mechanism for releasing the aromatic substances will now be described with reference to FIG. 7 and FIG. 8. FIG. 7 is a view of the folding type portable telephone in a folded state, where aroma releasing open/close valve 108 of the face panel is pushed and blocked by spring 110 fixed to spring press fixing part 111 so that the aromatic substances are not released. FIG. 8 is a view in which the folding type portable telephone is opened, where aroma releasing open/close valve 108 of the face panel is pressed against hinge projection 107 fixed to hinge 103 to release the aromatic substances.

Third Embodiment

Figure 9:
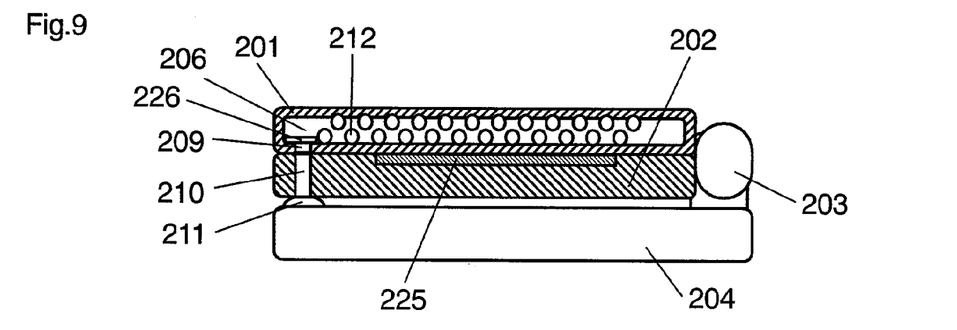
FIG. 9 is a partial cross sectional view of a folding type portable telephone according to a third embodiment of the present invention in a folded state seen from the side.
Figure 10:
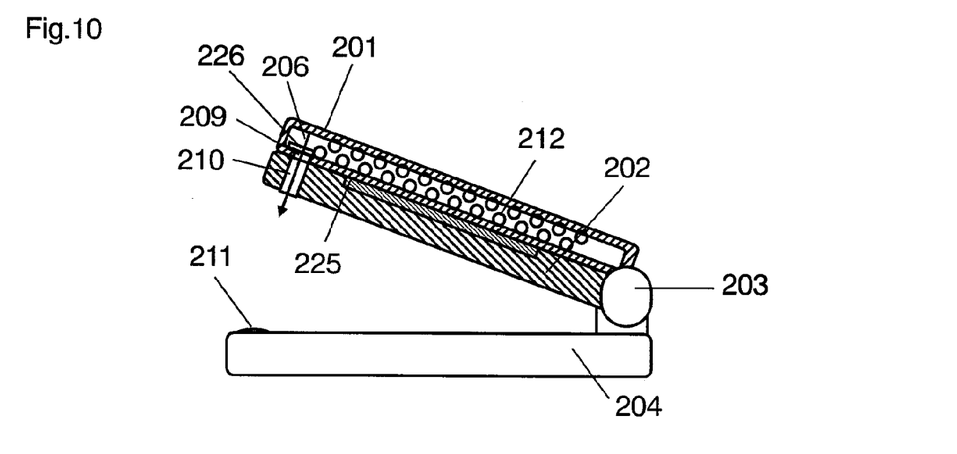
FIG. 10 is a partial cross sectional view of the folding type portable telephone according to the third embodiment of the present invention in a halfway opened state seen from the side.
Figure 11:
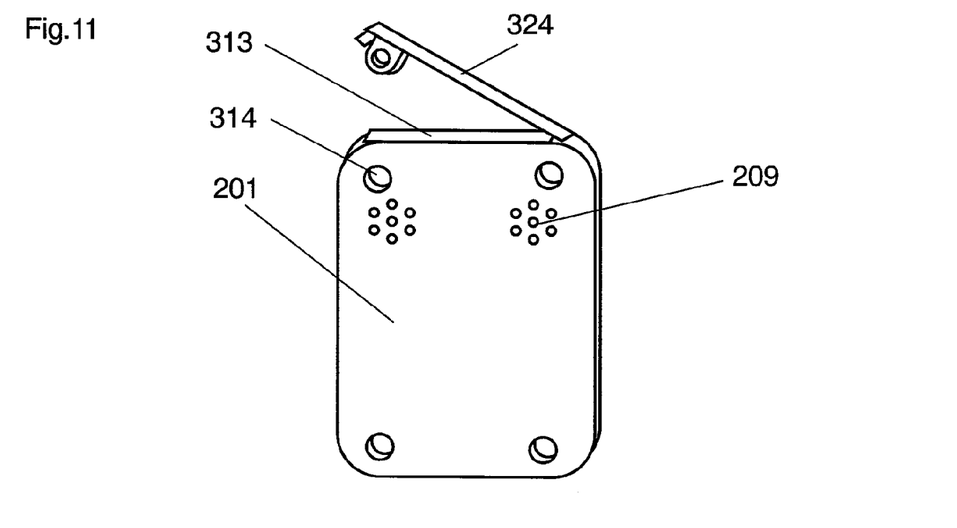
FIG. 11 is a perspective view of the side facing a housing side of a face panel in the third embodiment of the present invention.

FIG. 9 to FIG. 11 are views showing a third embodiment of a mobile terminal using an aromatic substance accommodating face panel according to the present invention, where the present invention is applied to a folding type portable telephone. FIG. 9 is a partial cross sectional view of the folding type portable telephone in a folded state seen from the side. FIG. 10 is a partial cross sectional view of the folding type portable telephone in a halfway opened state seen from the side. FIG. 11 is a perspective view of the side facing the housing side of the face panel.

In FIG. 9 to FIG. 11, face panel 201 has a hollow structure, and granulated aromatic substances 212 are accommodated in aromatic substance accommodating unit 206. Transparent or semi-transparent material is used for face panel 201, so that the external image of the folding type portable telephone can be changed by the coloring of granulated aromatic substances 212.

Face panel 201 has a structure of being fixed to upper housing 202.

The color of face panel 101 becomes brighter by arranging light emitting body 225 on face panel 201 surface side of housing 202. Light emitting body 225 may be lighted when receiving a call, during the call, or in conjunction with a timer or the like.

Upper housing 202 serving as the first housing and lower housing 204 serving as the second housing are supported in a freely rotating manner by hinge 203, where upper housing 202 and lower housing 204 are opened and closed by the rotational movement of hinge 203. Aroma releasing holes 209 of the face panel are opened on the surface facing upper housing 202 of face panel 201, and pass-through hole 210 of the upper housing is opened in upper housing 202 in correspondence to aroma releasing hole 209 of the face panel. Aromatic substances transmissive mesh sheet 226 is obtained by forming a mesh with air permeability to a sheet form, so that entering of dust and water droplets from the outside is prevented and at the same time the granulated aromatic substances are prevented from flowing outside. The route of releasing aromatic substances 212 is from aromatic substance accommodating unit 206, passed through aromatic substances transmissive mesh sheet 26 and aroma releasing hole 209 of the face panel, and released to the outside from pass-through hole 210 of the upper housing.

As shown in FIG. 9, when the folding type portable telephone is closed, pass-through hole 210 of the upper housing is blocked by spacer 211 fixed to lower housing 204, thereby suppressing the release of fragrance.

As shown in FIG. 10, when the folding type portable telephone is opened, granulated aromatic substances 212 pass through aroma releasing hole 209 of the face panel to be released to the outside from pass-through hole 210 of the upper housing structurally separated from other electronic components. The material of spacer 211 may be rubber, silicon, or the like other than polycarbonate resin (PC resin) and polycarbonate ABS resin (PC-ABS resin). In addition to adjusting the release of the aroma, the purpose of spacer 211 is also to prevent scratches from being made on the liquid crystal surface glass by keys.

As shown in FIG. 11, the aromatic substances can be easily replaced by arranging aromatic substance insertion lid 324 of the face panel and aromatic substance insertion port 313 of the face panel at one part on the outer periphery of the side surface of face panel 201. The aromatic substances may be in a granulated form, paper form, or solid form. Screw hole 314 of the face panel is a hole for fixing to upper housing 202 of FIG. 9 or FIG. 10, and is opened in plurals. Screw hole 314 of the face panel and the screw hole of aromatic substance insertion lid 324 are commonly fastened and locked with a screw. An effect of not being openable is obtained by fixing with a screw.

As shown in FIG. 9 and FIG. 10, since aroma releasing hole 209 of the face panel is arranged in the direction of the upper housing side of the portable telephone, the release of aroma can be controlled in cooperation with the open/close operation in the case of the folding type portable telephone, which is economical.

Fourth Embodiment

FIGS. 12 to 17 are views showing a fourth embodiment of a mobile terminal using an aromatic substance accommodating face panel according to the present invention, where the present invention is applied to the folding type portable telephone. The fourth embodiment describes a folding type portable telephone, but the shape of the portable telephone may be straight type, slide type, or rotating type.

Figure 12:
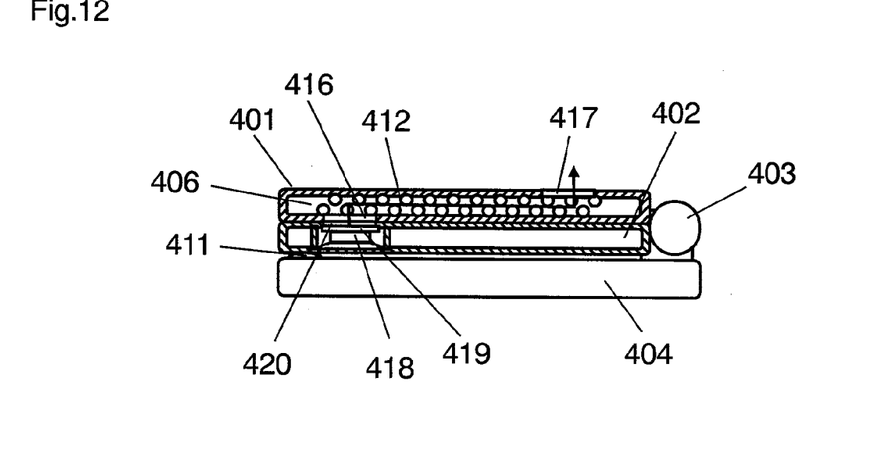
FIG. 12 is a partial cross sectional view of a folding type portable telephone according to a fourth embodiment of the present invention in a folded state seen from the side.
Figure 13:
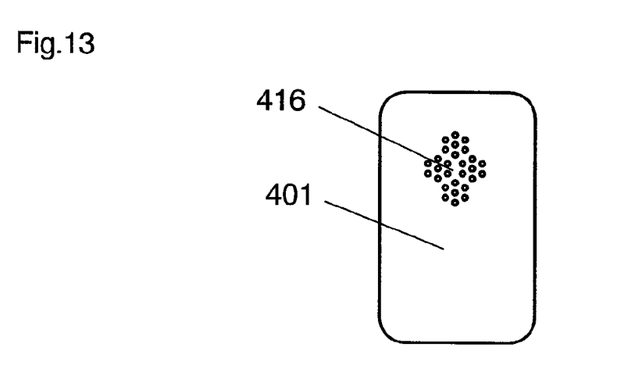
FIG. 13 is a plan view of the side facing the housing side of the face panel according to the fourth embodiment of the present invention.
Figure 14:
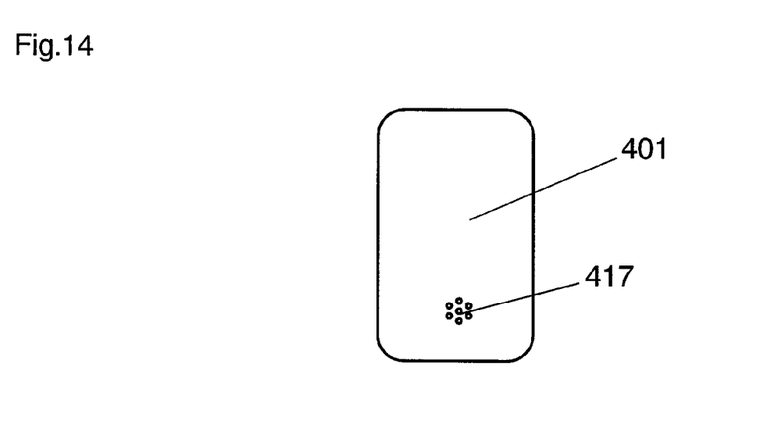
FIG. 14 is a plan view of the side facing the external side of the face panel according to the fourth embodiment of the present invention.

FIG. 12 is a partial cross sectional view of the folding type portable telephone in a folded state seen from the side. FIG. 13 is a plan view of the side facing the housing side of the face panel. FIG. 14 is a plan view of the side facing the external side of the face panel. In FIGS. 12 to 14, face panel 401 has a hollow structure, where granulated aromatic substances 412 are accommodated in aromatic substance accommodating unit 406. Transparent or semi-transparent material is used for face panel 401, so that the external image of the folding type portable telephone can be changed by the coloring of granulated aromatic substances 412. Face panel 401 has a structure of being fixed to upper housing 402.

Upper housing 402 serving as the first housing and lower housing 404 serving as the second housing are supported in a freely rotating manner by hinge 403, and upper housing 402 and lower housing 404 are opened and closed by the rotational movement of hinge 403. Sounding body 418 is fixed in upper housing 402, and is used for ring tones, music playing sounds, alarms, and the like. As a principle for releasing aroma, air vibration is transmitted through air vibration transmission hole 416 of the face panel from aromatic substance shield sheet 419 and air vibration transmitting hole 420 of upper housing, and passed through aromatic substance accommodating unit 406, thereby releasing the aroma from aroma releasing hole 417 of the face panel by the operation of sounding body 418. In the present invention, the aromatic substance shield sheet is arranged from sounding body 418 to air vibration transmitting hole 420 of housing and air vibration transmission hole 416 of the aromatic substance accommodating face panel. Therefore, the aromatic substance shield sheet is interposed for a spatial bonding with the sounding body, whereby aroma does not enter the sounding body side.

In the present invention, the release of aroma is controlled by actively using the air vibration of sounding body 418. Normally, the air vibration can be transmitted more in the low region than in the high region if the sound pressure is the same. Utilizing this effect, a control of generating more sound in the low region is actively performed to strongly cause release of aroma.

Figure 15:
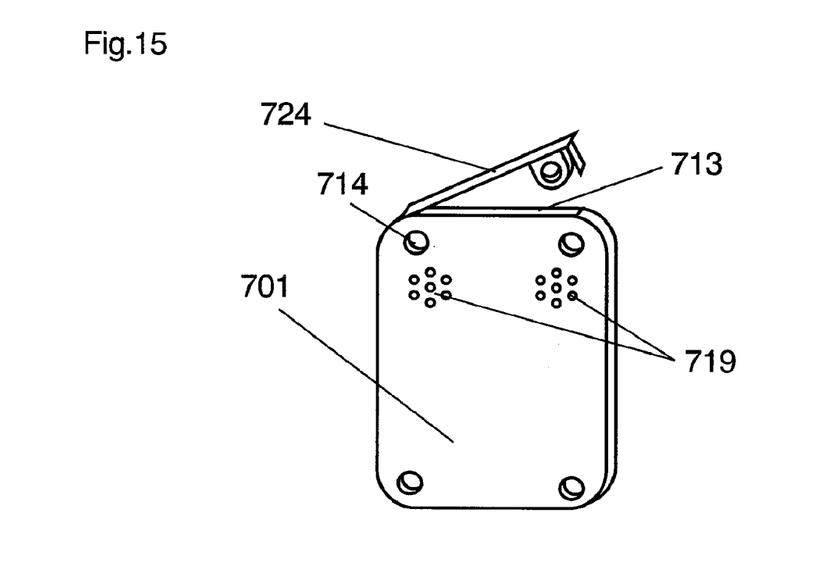
FIG. 15 is a perspective view of the side facing the housing side of another face panel according to the fourth embodiment of the present invention.
Figure 16:
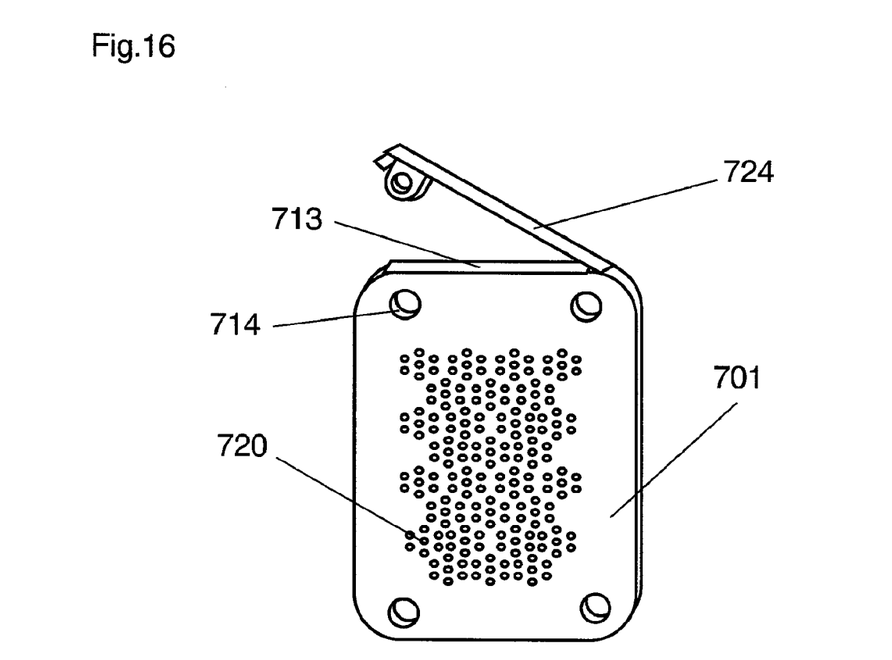
FIG. 16 is a perspective view of the side facing the external side of another face panel according to the fourth embodiment of the present invention.

FIGS. 15 and 16 show the front and the back of face panel 701 of a configuration of the aroma releasing accommodating face panel in which two sounding bodies 418 are arranged. Stereo speakers are being widespread used in recent portable telephones, and the content herein corresponds thereto. FIG. 15 is a perspective view of the side facing the housing side of face panel 701. Air vibration transmission hole 719 of the face panel for transmitting the air vibration from the housing side is formed. FIG. 16 is a perspective view of the side facing the external side of the face panel. Aroma releasing hole 720 of the face panel for transmitting the aroma to the outside is opened. The air vibration from the housing side is inputted from air vibration transmission hole 719 of FIG. 15, and outputted from aroma releasing hole 720 of the face panel of FIG. 16 through the aromatic substance accommodating unit inside face panel 701. Aromatic substance insertion port 713 of the face panel for replacing the aromatic substances and aromatic substance insertion lid 724 of the face panel are arranged on the periphery of face panel 701. As a feature of the configuration, a hole is opened on both the front and the back of face panel 701, and the function of the respective holes on the front and the back are divided to an input side and an output side.

Figure 17:
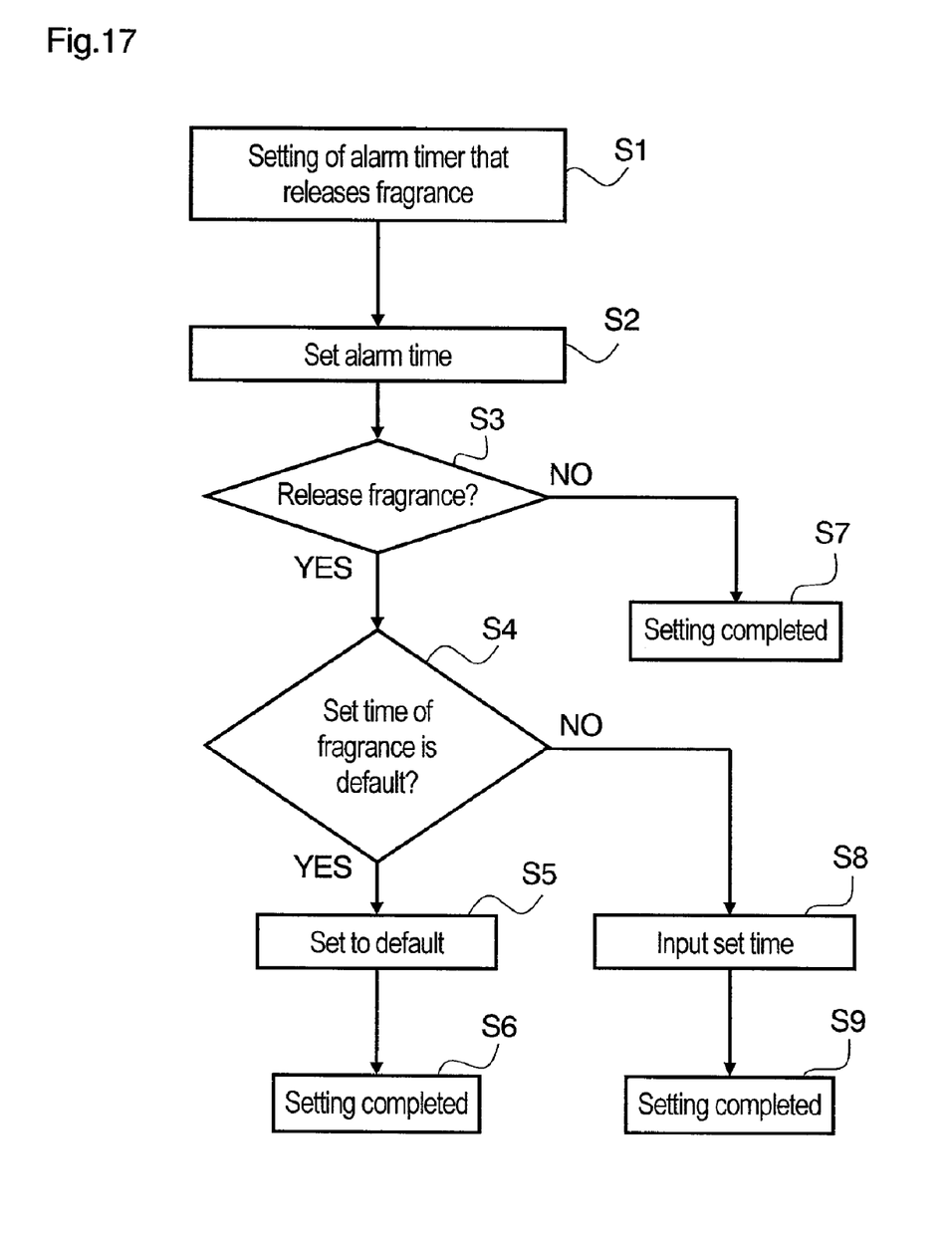
FIG. 17 shows a flowchart of an alarm timer that releases fragrance according to the fourth embodiment of the present invention.

The present invention provides a function of releasing aroma at a predetermined time by driving the sounding body with an alarm timer. FIG. 17 shows a flowchart of setting an alarm timer that releases fragrance. First, a setting of an alarm timer that releases fragrance is selected (step S1). Next, the setting of the alarm time is performed (step S2), and thereafter, setting of whether or not to release fragrance is performed (step S3). In the setting of releasing fragrance, a time to release fragrance is set separate from the alarm time (step S4). The time to release fragrance is branched to setting to a default set in advance (step S5), and setting to other times (step S8). For instance, when the default is set to 30 minutes, a timer for releasing the fragrance is set to thirty minutes before the alarm time. When inputting the set time in step S8 instead of the default, a user can freely set the operation until transitioning to the alarm sound operation from the time of setting. The sound in time of setting to release fragrance uses a frequency of low region that is less likely to be heard by ear of about lower than or equal to 50 Hz.

When generating an alarm sound with the alarm timer etc. of the present invention, one can wake up in a nice smell by operating the sound of low region for strongly generating the aroma at a time before the time set in advance.

In mobile terminals such as the portable telephone including a vibrator etc. for incoming annunciation, even though not premised on the sounding body, the aromatic substance accommodating face panel in which the aroma releasing hole is formed on one surface and the air vibration transmission hole for transmitting air vibration is formed on the other surface may be fixed to the housing to release aroma by picking up vibration of the housing from the air vibration transmission hole.

Fifth Embodiment

Figure 18:
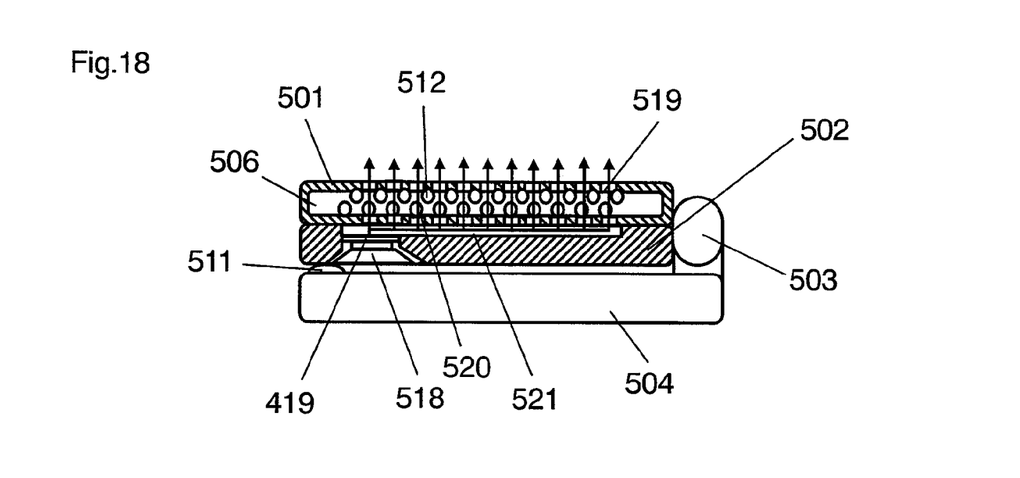
FIG. 18 is a partial cross sectional view of a folding type portable telephone according to a fifth embodiment of the present invention in a folded state seen from the side.
Figure 19:
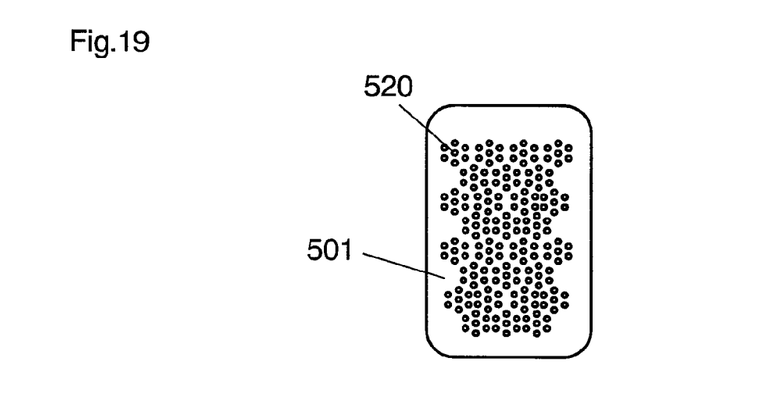
FIG. 19 is a plan view of the side facing the housing side of the face panel according to the fifth embodiment of the present invention.
Figure 20:
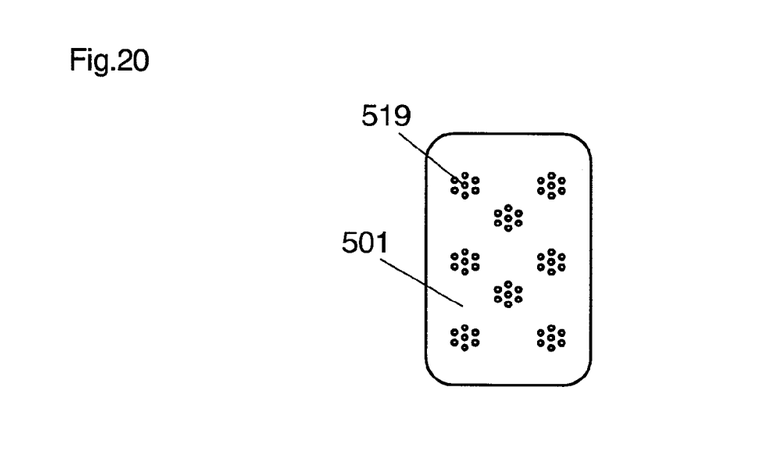
FIG. 20 is a plan view of the side facing the external side of the face panel according to the fifth embodiment of the present invention.

FIGS. 18 to 20 are views showing a fifth embodiment of the mobile terminal using an aromatic substance accommodating face panel according to the present invention, where the present invention is applied to the folding type portable telephone. The fifth embodiment describes a folding type portable telephone, but the shape of the portable telephone may be straight type, slide type, or rotating type.

FIG. 18 is a cross sectional view of the folding type portable telephone in the folded state seen from the side. FIG. 19 is a plan view of the side facing the housing side of the face panel. FIG. 20 is a plan view of the side facing the external side of the face panel. In FIGS. 18 to 20, face panel 501 has a hollow structure, and granulated aromatic substances 512 are accommodated in aromatic substance accommodating unit 506. Transparent or semi-transparent material is used for face panel 501, so that the external image of the folding type portable telephone can be changed by the coloring of granulated aromatic substances 512. Face panel 501 has a structure of being fixed to upper housing 502.

Upper housing 502 serving as the first housing and lower housing 504 serving as the second housing are supported in a freely rotating manner by hinge 503, where upper housing 502 and lower housing 504 are opened and closed by the rotational movement of hinge 503. Spacer 511 fixed to lower housing 504 is arranged to prevent scratches from being made on the liquid crystal screen glass by keys.

Sounding body 518 is fixed in upper housing 502, and is used for ring tones, music playing sounds, alarms, and the like. As a principle for releasing aroma, air vibration is transmitted to entire air vibration transmitting space 521 at a gap portion of face panel 501 and upper housing 502, and passed through air vibration transmission hole 520 of the face panel, and through aromatic substance accommodating unit 506, thereby releasing the aroma from aroma releasing hole 519 of the face panel by the operation of sounding body 518.

Therefore, the aroma can be more strongly released from the entire front surface of face panel 501. Regarding the effect of using sounding body 518, when generating an alarm sound with an alarm timer etc., one can wake up in a nice smell by operating the sound of low region for strongly generating the aroma at a time before the time set in advance.

Sixth Embodiment

FIGS. 21 to 24 are views showing a sixth embodiment of the mobile terminal using an aromatic substance accommodating face panel according to the present invention, where the present invention is applied to the folding type portable telephone.

Figure 21:
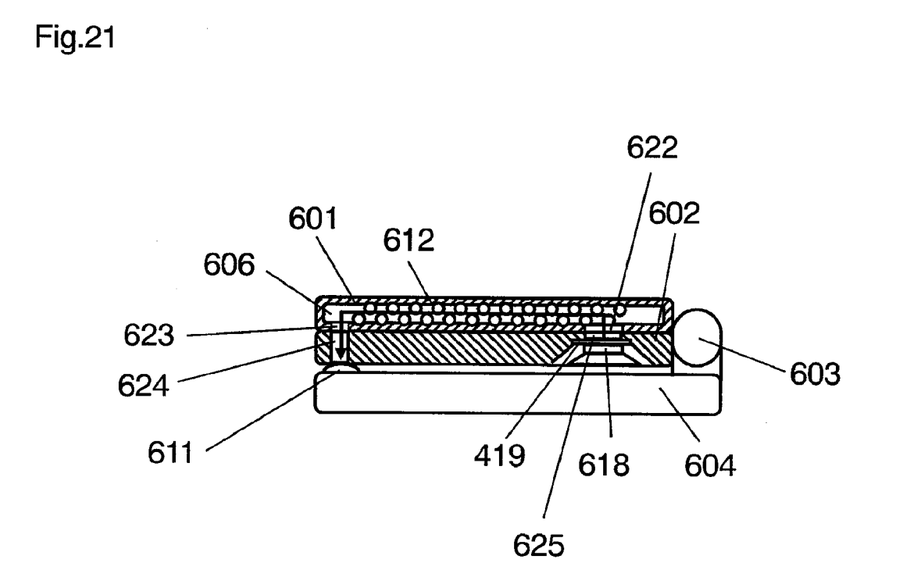
FIG. 21 is a partial cross sectional view of a folding type portable telephone according to a sixth embodiment of the present invention in a folded state seen from the side.
Figure 22:
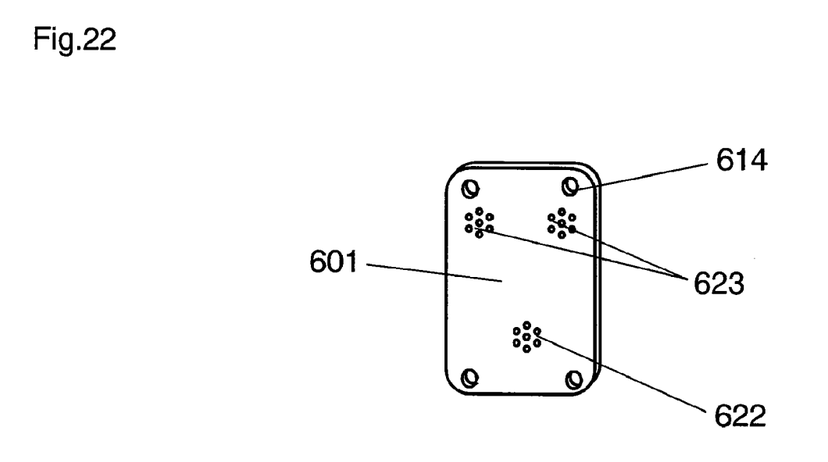
FIG. 22 is a perspective view of the side facing the housing side of the face panel according to the sixth embodiment of the present invention.

FIG. 21 is a partial cross sectional view of the folding type portable telephone in a folded state seen from the side. FIG. 22 is a perspective view of the side facing the housing side of the face panel. In FIGS. 21 and 22, face panel 601 has a hollow structure, and granulated aromatic substances 612 are accommodated in aromatic substance accommodating unit 606. Transparent or semi-transparent material is used for face panel 601, so that the external image of the folding type portable telephone can be changed by the coloring of granulated aromatic substances 612. Face panel 601 has a structure of being fixed to upper housing 602.

In the sixth embodiment, two operations of the operation of sounding body 618 and the operation of opening the folding type portable telephone from the closed state cooperate to release granulated aromatic substances 612. This is a combination of the third embodiment and the fourth embodiment described above.

The feature lies in that aroma releasing hole 623 of the face panel and air vibration transmission hole 622 of the face panel are in the same plane of face panel 601 as shown in FIG. 21. As a principle of releasing the aroma, the air vibration is transmitted from aromatic substance shield sheet 419 and air vibration transmitting hole 625 of upper housing through air vibration transmission hole 622 of the face panel, passed through aromatic substance accommodating unit 606, thereby releasing the aroma from aroma releasing hole 623 of the face panel through pass-through hole 624 of upper housing by the operation of sounding body 618.

Regarding the effect of using sounding body 618, when generating an alarm sound with an alarm timer etc., one can wake up in a nice smell by opening the folding type portable telephone in advance and operating the sound of low region for strongly generating the aroma at a time before the time set in advance. However, the generation of the aroma is stopped if the folding type portable telephone is closed.

Figure 23:
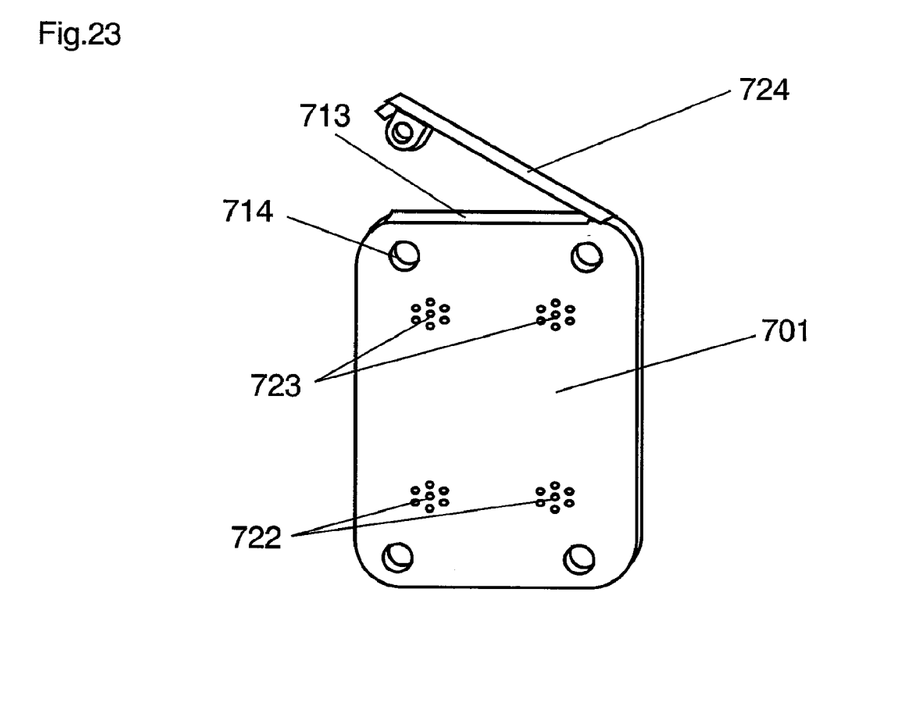
FIG. 23 is a perspective view of the side facing the housing side of another face panel according to the sixth embodiment of the present invention.
Figure 24:
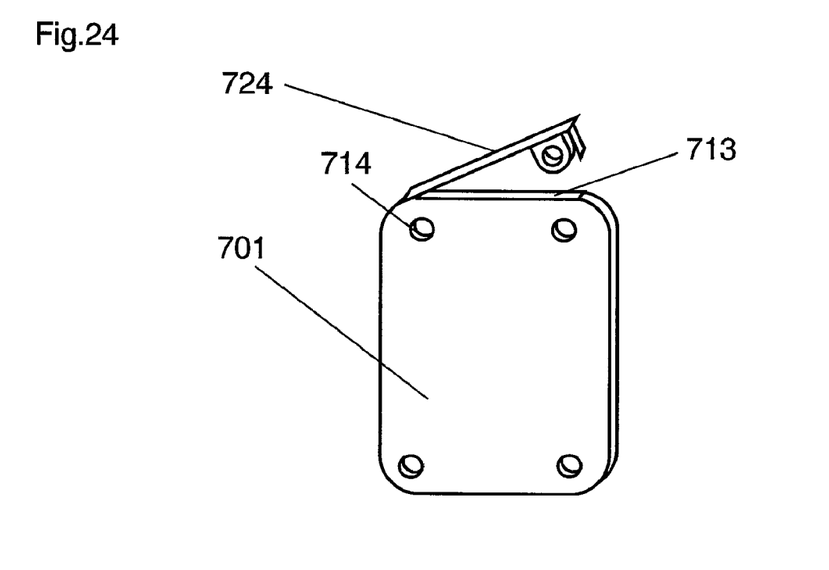
FIG. 24 is a perspective view of the side facing the external side of another face panel according to the sixth embodiment of the present invention.

FIGS. 23 and 24 show the front and the back of face panel 701 of a configuration of a face panel with aroma releasing function in which two sounding bodies 618 are arranged. FIG. 23 is a perspective view of the side facing the housing side of face panel 701. The feature lies in that air vibration transmission hole 722 of the face panel for transmitting air vibration from the housing side and aroma releasing hole 723 of the face panel for transmitting the aroma to the outside are opened on the same surface. FIG. 24 is a perspective view of the side facing the external side of the face panel. The holes for releasing the aroma are not opened on the external side of face panel 701. Aromatic substance insertion port 713 of the face panel for replacing the aromatic substances and aromatic substance insertion lid 724 of the face panel are arranged on the periphery of face panel 701.

INDUSTRIAL APPLICABILITY

The present invention is applicable to a mobile terminal with aroma releasing function in which the aroma can be changed according to TPO by using the face panel as the aromatic substance accommodating face panel in mobile terminals such as a portable telephone, a PDA, a music player and a game equipment attached with a removable face panel.

The invention claimed is:
1. A mobile terminal comprising:
a first housing;
a second housing;
a hinge for connecting the first housing and the second housing rotatably;
a projection formed on the hinge;
an aromatic substance accommodating face panel removably attached to the first housing or the second housing, the aromatic substance accommodating face panel having a hollow structure;
an aroma releasing hole for releasing an aroma and formed on a surface of the panel; and
an open/close valve for opening and closing the hollow structure with respect to an external space and formed on the surface of the panel;
wherein the hinge rotates, so that the projection of the hinge controls the open/close valve of the aromatic substance accommodating face panel to release the aroma from the aroma releasing hole at the surface of the aromatic substance accommodating face panel.

* * * * *